United States Patent [19]

Gurewich

[11] Patent Number: 5,626,841
[45] Date of Patent: May 6, 1997

[54] USE OF INTRA-PLATELET UROKINASE-TYPE PLASMINOGEN ACTIVATORS FOR LONG-TERM INHIBITION OF THROMBOSIS

[76] Inventor: Victor Gurewich, 11 Reservoir St., Cambridge, Mass. 02138

[21] Appl. No.: 254,922

[22] Filed: Jun. 7, 1994

Related U.S. Application Data

[63] Continuation-in-part of Ser. No. 14,207, Feb. 5, 1993, abandoned.

[51] Int. Cl.$^6$ .............................. A61K 38/49; C12N 9/64; C12N 9/72
[52] U.S. Cl. .................................... 424/94.63; 424/94.64; 435/215; 435/226
[58] Field of Search ....................... 424/94.63, 94.64; 435/212, 215, 216; 514/12

[56] References Cited

U.S. PATENT DOCUMENTS

| Re. 32,271 | 10/1986 | Husain et al. | 435/215 |
| 5,055,295 | 10/1991 | Welzel et al. | 424/94.2 |
| 5,188,829 | 2/1993 | Kobayashi | 424/94.63 |

FOREIGN PATENT DOCUMENTS

0395918A2  11/1990  European Pat. Off. .

OTHER PUBLICATIONS

Gurewich, V. et al., "The Selective Uptake of High Molecular Weight Urokinase-Type Plasminogen Activator by Human Platelets", *Fibrinolysis* 9:188–195 (1995).

Badylak et al., *Thromb. Res.*, 52:294–312 (1988).
Bode et al., *Circulation*, 84:805–813 (1991).
Declerck et al., *Thromb. Haemostas.*, 67:95–100 (1992).
Eguchi et al., *J. Biochem. (Tokyo)*, 108:72–19 (1990).
Gurewich et al., *Thromb. Res.*, 44:217–228 (1986).
Gurewich, *Sem. Thromb. Hemostasis*, 15:123–128 (1989).
Miyake et al., *J. Biochem. (Tokyo)*, 104:643–647 (1988).
Park et al., *Blood*, 73:1421–1425 (1989).
Rao et al., *Thromb. Res.*,62:319–334 (1991).
Roberts, *Amer. J. Cardiol.*, 67:1A–2A (1991).
Vaughan et al., *Fibrinolysis*, 4:141–146 (1990).
Vaughan et al., *J. Biol. Chem.*, 264:15869–15874 (1989).

*Primary Examiner*—Dian C. Jacobson
*Attorney, Agent, or Firm*—Fish & Richardson P.C.

[57] ABSTRACT

A method of adjunctive therapy to inhibit reocclusions in a patient, e.g., after thrombolytic therapy or angioplasty, by administering to the patient a bolus of an amount of purified pro-urokinase ("pro-UK") that inhibits the formation of occlusive thrombi without inducing a systemic effect in the patient, the pro-UK is administered after the completion of the thrombolytic treatment and periodically thereafter for the duration of therapy, and becomes incorporated into the outer membrane of the platelets of the patient, thereby increasing the $T_{1/2}$ of the pro-UK in plasma, which is about 7 to 8 minutes, to about 4 to 5 days, and inhibiting reocclusion without inducing a systemic effect.

13 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 1233
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
AGC  AAT  GAA  CTT  CAT  CAA  GTT  CCA  TCG  AAC  TGT  GAC  TGT  CTA  AAT  GGA       48
Ser  Asn  Glu  Leu  His  Gln  Val  Pro  Ser  Asn  Cys  Asp  Cys  Leu  Asn  Gly
               5                        10                       15

GGA  ACA  TGT  CTG  TCC  AAC  AAG  TAC  TTC  TCC  AAC  ATT  CAC  TGG  TGC  AAC       96
Gly  Thr  Cys  Val  Ser  Asn  Lys  Tyr  Phe  Ser  Asn  Ile  His  Trp  Cys  Asn
                20                        25                       30

TGA  CCA  AAG  AAA  TTC  GGA  GGG  CAG  CAC  TGT  GAA  ATA  GAT  AAG  TCA  AAA      144
Cys  Pro  Lys  Lys  Phe  Gly  Gly  Gln  His  Cys  Glu  Ile  Asp  Lys  Ser  Lys
          35                             40                  45

ACC  TGC  TAT  GAG  GGG  AAA  GGT  CAC  TTT  TAC  CGA  GGA  AAG  GCC  AGC  ACT      192
Thr  Cys  Tyr  Glu  Gly  Asn  Gly  His  Phe  Tyr  Arg  Gly  Lys  Ala  Ser  Thr
     50                        55                      60

GAC  ACC  ATG  GGC  CGG  CCC  TGC  CTG  CCC  TGG  AAC  TCT  GCC  ACT  GTC  CTT      240
Asp  Thr  Met  Gly  Arg  Pro  Cys  Leu  Pro  Trp  Asn  Ser  Ala  Thr  Val  Leu
65                       70                       75                        80

CAG  CAA  ACG  TAC  CAT  GCC  CAC  AGA  TCT  GAT  GCT  CTT  CAG  CTG  GGC  CTG      288
Gln  Gln  Thr  Tyr  His  Ala  His  Arg  Ser  Asp  Ala  Leu  Gln  Leu  Gly  Leu
                    85                        90                       95

GGG  AAA  CAT  AAT  TAC  TGC  AGG  AAC  CCA  GAC  AAC  CGG  AGG  CGA  CCC  TGG      336
Gly  Lys  His  Asn  Tyr  Cys  Arg  Asn  Pro  Asp  Asn  Arg  Arg  Arg  Pro  Trp
               100                      105                      110
```

| | | | | | | | | | | | | | | | |
|---|---|---|---|---|---|---|---|---|---|---|---|---|---|---|---|
| TGC | TAT | GTG | CAG | GTG | GGC | CTA | AAG | CCG | CTT | GTC | CAA | GAG | TGC | ATG | GTG | 384
| Cys | Tyr | Val | Gln | Val | Gly | Leu | Lys | Pro | Leu | Val | Gln | Glu | Cys | Met | Val |
| | | 115 | | | | 120 | | | | | 125 | | | | |
| CAT | GAC | TGC | GCA | GAT | GGA | AAA | AAG | CCC | TCC | TCT | CCT | CCA | GAA | GAA | TTA | 432
| His | Asp | Cys | Ala | Asp | Gly | Lys | Lys | Pro | Ser | Ser | Pro | Pro | Glu | Glu | Leu |
| 130 | | | | | 135 | | | | | 140 | | | | | |
| AAA | TTT | CAG | TGT | GGC | CAA | AAG | ACT | CTG | AGG | CCC | CGC | TTT | AAG | ATT | ATT | 480
| Lys | Phe | Gln | Cys | Gly | Gln | Lys | Thr | Leu | Arg | Pro | Arg | Phe | Lys | Ile | Ile |
| 145 | | | | | 150 | | | | | 155 | | | | | 160 |
| GGG | GGA | GAA | TTC | ACC | ACC | ATC | GAG | AAC | CAG | CCC | TGG | TTT | GCG | GCC | ATC | 528
| Gly | Gly | Glu | Phe | Thr | Thr | Ile | Glu | Asn | Gln | Pro | Trp | Phe | Ala | Ala | Ile |
| | | | | 165 | | | | | 170 | | | | | 175 | |
| TAC | AGG | AGG | CAC | CGG | GGG | GGC | TCT | GTC | ACC | TAC | GTG | TGT | GGA | GGC | AGC | 576
| Tyr | Arg | Arg | His | Arg | Gly | Gly | Ser | Val | Thr | Tyr | Val | Cys | Gly | Gly | Ser |
| | | | 180 | | | | | 185 | | | | | 190 | | |
| CTC | ATC | AGC | CCT | TGC | TGG | GTG | ATC | AGC | GCC | ACA | CAC | TGC | TTC | ATT | GAT | 624
| Leu | Ile | Ser | Pro | Cys | Trp | Val | Ile | Ser | Ala | Thr | His | Cys | Phe | Ile | Asp |
| | | | 195 | | | | 200 | | | | | 205 | | | |
| TAC | CCA | AAG | AAG | GAG | GAC | TAC | ATC | GTC | TAC | CTG | GGT | CGC | TCA | AGG | CTT | 672
| Tyr | Pro | Lys | Lys | Glu | Asp | Tyr | Ile | Val | Tyr | Leu | Gly | Arg | Ser | Arg | Leu |
| | 210 | | | | | 215 | | | | | 220 | | | | |
| AAC | TCC | AAC | ACG | CAA | GGG | GAG | ATG | AAG | TTT | GAG | GTG | GAA | AAC | CTC | ATC | 720
| Asn | Ser | Asn | Thr | Gln | Gly | Glu | Met | Lys | Phe | Glu | Val | Glu | Asn | Leu | Ile |
| 225 | | | | | 230 | | | | | 235 | | | | | 240 |
| CTA | CAC | AAG | GAC | TAC | AGC | GCT | GAC | ACG | CTT | GCT | CAC | CAC | AAC | GAC | ATT | 768
| Leu | His | Lys | Asp | Tyr | Ser | Ala | Asp | Thr | Leu | Ala | His | His | Asn | Asp | Ile |
| | | | | 245 | | | | | 250 | | | | | 255 | |
| GCC | TTG | CTG | AAG | ATC | CGT | TCC | AAG | GAG | GGC | AGG | TGT | GCG | CAG | CCA | TCC | 816
| Ala | Leu | Leu | Lys | Ile | Arg | Ser | Lys | Glu | Gly | Arg | Cys | Ala | Gln | Pro | Ser |
| | | | 260 | | | | | 265 | | | | | 270 | | |
| CGG | ACT | ATA | CAG | ACC | ATC | TGC | CTG | CCC | TCG | ATG | TAT | AAC | GAT | CCC | CAG | 864
| Arg | Thr | Ile | Gln | Thr | Ile | Cys | Leu | Pro | Ser | Met | Tyr | Asn | Asp | Pro | Gln |
| | | 275 | | | | | 280 | | | | | 285 | | | |
| TTT | GGC | ACA | AGC | TGT | GAG | ATC | ACT | GGC | TTT | GGA | AAA | GAG | AAT | TCT | ACC | 912
| Phe | Gly | Thr | Ser | Cys | Glu | Ile | Thr | Gly | Phe | Gly | Lys | Glu | Asn | Ser | Thr |
| | 290 | | | | | 295 | | | | | 300 | | | | |
| GAC | TAT | CTC | TAT | CCG | GAG | CAG | CTG | AAG | ATG | ACT | GTT | GTG | AAG | CTG | ATT | 960
| Asp | Tyr | Leu | Tyr | Pro | Glu | Gln | Leu | Lys | Met | Thr | Val | Val | Lys | Leu | Ile |
| 305 | | | | | 310 | | | | | 315 | | | | | 320 |
| TCC | CAC | CGG | GAG | TGT | CAG | CAG | CCC | CAC | TAC | TAC | GGC | TCT | GAA | GTC | ACC | 1008
| Ser | His | Arg | Glu | Cys | Gln | Gln | Pro | His | Tyr | Tyr | Gly | Ser | Glu | Val | Thr |
| | | | | 325 | | | | | 330 | | | | | 335 | |
| ACC | AAA | ATG | CTG | TGT | GCT | GCT | GAC | CCA | CAG | TGG | AAA | ACA | GAT | TCC | TGC | 1056
| Thr | Lys | Met | Leu | Cys | Ala | Ala | Asp | Pro | Gln | Trp | Lys | Thr | Asp | Ser | Cys |
| | | | 340 | | | | | 345 | | | | | 350 | | |
| CAG | GGA | GAC | TCA | GGG | GGA | CCC | CTC | GTC | TGT | TCC | CTC | CAA | GGC | CGC | ATG | 1104
| Gln | Gly | Asp | Ser | Gly | Gly | Pro | Leu | Val | Cys | Ser | Leu | Gln | Gly | Arg | Met |
| | | 355 | | | | | 360 | | | | | 365 | | | |
| ACT | TTG | ACT | GGA | ATT | GTG | AGC | TGG | GGC | CGT | GGA | TGT | GCC | CTG | AAG | GAC | 1152
| Thr | Leu | Thr | Gly | Ile | Val | Ser | Trp | Gly | Arg | Gly | Cys | Ala | Leu | Lys | Asp |
| | 370 | | | | | 375 | | | | | 380 | | | | |
| AAG | CCA | GGC | GTC | TAC | ACG | AGA | GTC | TCA | CAC | TTC | TTA | CCC | TGG | ATC | CGC | 1200
| Lys | Pro | Gly | Val | Tyr | Thr | Arg | Val | Ser | His | Phe | Leu | Pro | Trp | Ile | Arg |
| 385 | | | | | 390 | | | | | 395 | | | | | 400 |
| AGT | CAC | AAC | AAG | GAA | GAG | AAT | GGC | CTG | GCC | CTC | | | | | | 1233
| Ser | His | Thr | Lys | Glu | Glu | Asn | Gly | Leu | Ala | Leu | | | | | |
| | | | | 405 | | | | | 410 | | | | | | |

USE OF INTRA-PLATELET UROKINASE-TYPE PLASMINOGEN ACTIVATORS FOR LONG-TERM INHIBITION OF THROMBOSIS

This application is a continuation-in-part of application U.S. Ser. No. 08/014,207, filed Feb. 5, 1993, now abandoned.

BACKGROUND OF THE INVENTION

The invention relates to the administration of urokinase-type plasminogen activators ("u-PA"), such as pro-urokinase ("pro-UK"), to patients.

Thrombolytic therapy, e.g., with streptokinase ("SK") or tissue-type plasminogen activator ("tPA"), is widely used to dissolve potentially life-threatening blood clots, e.g., after acute myocardial infarction. Angioplasty, e.g., percutaneous transluminal coronary angioplasty ("PTCA"), is used to open coronary artery stenoses. Such therapies are associated with an undesirably high rate of reocclusion, and often reinfarction, which can occur within hours after successful lysis, and substantially attenuates the therapeutic effect. For example, reocclusions occur in about 29% of patients treated with tPA, Morrie et al., Am Heart, 122: 375–380 (1991), Kalbfleisch, et al., Am. J. Cardiol., 69: 1120–1127 (1992), and in about 10% of patients treated with SK, Yusuf et al., J.A.M.A., 260: 2088–2093 (1988). In addition, about 30% of the stenoses opened by PTCA reocclude within three months.

To counteract such undesirable reocclusions, various adjunctive therapies have been developed for use after thrombolysis. For example, aspirin, heparin, thrombin inhibitors, platelet inhibitors, monoclonal antibodies to platelet glycoprotein IIb/IIIa, and activated protein C have all been identified as potential agents for use in adjunctive strategies. In addition, β-blockers, calcium antagonists, angiotensin-converting enzyme inhibitors, and nitrates also may be useful adjuncts to thrombolytic therapy.

Adjunctive agents such as high dose heparin, hirudin analogs, or anti-platelet agents can be associated with hemorrhagic complications, e.g., systemic bleeding. Moreover, these adjunctive therapies are expensive and complicate thrombolytic therapy, thereby compromising optimal early administration of the thrombolytic agents.

One such thrombolytic agent is pro-UK, or urinary-type plasminogen activator, which is a naturally occurring plasminogen activator consisting of a single-chain polypeptide made up of 411 amino acids; hence, pro-UK is also referred to as single chain urokinase-plasminogen activator ("scu-PA"). Pro-UK was first purified from urine, see U.S. Pat. No. Reissue 32,271, and has subsequently been produced by recombinant techniques. Pro-UK is a pro-enzyme which is converted into urokinase ("UK") by the action of plasmin. Once it enters the bloodstream, pro-UK is rapidly cleared from the plasma, and as described in, e.g., Collen et al. Am. J. Cardiol., 60: 431–434 (1987), has a half-life ($T_{1/2}$) of about eight minutes. Therefore, when used for therapeutic purposes, pro-UK is typically administered by infusion which, when terminated, is followed by rapid clearance of the drug from the plasma.

Pro-UK has been used in clinical trials for therapeutic thrombolysis, e.g., in patients with myocardial infarction, pulmonary embolism, or deep vein thrombosis. For example, U.S. Pat. No. 5,055,295 (Welzel et al.) describes the lysis of blood clots with combinations of pro-UK and UK in post-operative patients, and in patients who had a myocardial infarction or deep vein thrombi.

Bolus injections of pro-UK are associated with a short plasma half-life and the absence of fibrin clot binding. However, when preceded by a bolus of UK (2.5 mg) or tPA (5 mg), the thrombolytic effect of pro-UK is synergistically promoted, and lower rates of infusion of pro-UK are efficacious (40 mg/h instead of 60–80 mg/h). See, e.g., Gurewich et al., Thromb. Res., 44: 217–228 (1986).

Bolus injections of pro-UK (0.2–2 mg/kg) have been shown in one study to produce effective thrombolysis of arterial thrombi in dogs. Badylak et al., Thromb. Res., 52: 295–312 (1988). This study showed that the thrombolytic effect in the dogs lasted for at least 30 to 40 minutes despite a plasma $T_{1/2}$ of pro-UK of only 6 minutes. The reason for this effect was not known.

In the absence of a fibrin clot, pro-UK has been reported to be relatively inert below certain concentrations in the blood. For example, Gurewich, V., Sem. Thromb. Hemostasis, 15: 123–128 (1989) has reported that "little to no fibrinogen degradation [occurred] when less than 50 mg/hour of pure wild type pro-UK was infused" in clinical trials (p. 125). In the presence of a fibrin clot, pro-UK selectively activates any plasminogen associated with the clot. However, at higher doses, non-specific plasminogen activation can occur, which converts pro-UK to UK systemically and increases the risk of bleeding.

Although exogenous pro-UK induces fibrin-specific clot lysis in plasma in vitro and in vivo, the biological role of endogenous pro-UK is believed to be related to tissue remodeling, inflammation, and cell migration rather than fibrinolysis. See, e.g., Rohrlich et al., Annual Rep. Med. Chem., 14: 229–239 (1979), and Saksela, Biochim. Biophys. Acta., 823: 35–65 (1985). Moreover, antibodies that inhibit u-PA activity fail to inhibit the spontaneous lysis of fibrin clots in plasma, which was found to be due exclusively to tPA. See, e.g., Wun et al., J. Biol. Chem., 260: 5061–5066 (1985), and Gurewich et al., Fibrinolysis, 2: 143–149 (1988). Furthermore, according to Declerck et al., Thromb. Haemostas., 67: 95–100 (1992), the normal plasma concentration of pro-UK is less than 2 ng/ml.

Park et al., Blood, 73: 1421–1425 (1989), notes that trace amounts of pro-UK are associated with the outer leaflet of sonicated platelet membranes, however, the source of this pro-UK is not identified and no studies of the incorporation of exogenous pro-UK are presented. Vaughan et al., Fibrinolysis, 4: 141–146 (1990), identifies the presence of a u-PA receptor on platelets which does not bind tPA or low molecular weight UK. This receptor has a low affinity (~130 nM) for u-PA and is therefore considered to be of uncertain physiological relevance, because the normal concentration of u-PA in the blood is less than about 36 pM, or about 2 ng/ml of blood.

SUMMARY OF THE INVENTION

Applicant has discovered a new method of long-term inhibition of thrombosis, for example, as adjunctive therapy for use after thrombolysis or angioplasty, based on the finding that, in addition to blood plasma, an important reservoir for u-PA, e.g., pro-UK, is the blood platelet. Moreover, applicant has discovered that when a patient's blood is enriched with pro-UK in an amount below that which would cause a systemic effect, e.g., fibrinogenolysis and plasminemia, the patient's platelets rapidly incorporate significant amounts of pro-UK, enriching their normal content by about 100-fold.

The u-PA, e.g., pro-UK, does not dissociate from the platelets, even after acid washing, which indicates that it is not bound to a surface protein but rather is incorporated by the platelet, and in particular, by the platelet membrane. In contrast to pro-UK in plasma, the pro-UK in platelets is not cleared from the circulation, but remains in the bloodstream for as long as the platelets remain intact and in the circulation ($T_{1/2}$~4 to 5 days or longer).

As used herein, the term u-PA covers native, recombinant, and certain mutant forms of u-PA, e.g., pro-UK and forms of UK which are incorporated by platelets, and which can be administered to a patient without inducing a systemic effect. The term "purified pro-UK" covers pro-UK or pro-UK mutants which include the A-chain domain, which applicant has discovered is required for platelet incorporation. Since a forming thrombus is rich in thrombin, which inactivates pro-UK, a thrombin-resistant mutant (such as can be made by site-directed mutagenesis of Arg-156 to Alanine or Glycine) is preferred to obtain the maximum effect from the intra-platelet pro-UK.

As used herein, the term "systemic effect" covers a variety of undesirable, and potentially dangerous, conditions in the vascular system of a patient known to accompany the administration of thrombolytic agents such as tPA, SK, UK, or pro-UK in high doses. For example, the term includes fibrinogenolysis, plasminemia, and other interference with blood coagulation throughout the body.

Applicant has also found that this incorporation of u-PA by platelets is specific, in that it does not occur with tPA, SK, or low molecular weight UK ("LMW-UK"), but does occur with pro-UK and high molecular weight (~50–53 kDa) single or two-chain high molecular weight UK ("HMW-UK"), which indicates that incorporation is mediated by a domain on the A-chain of UK. This incorporation does not require carbohydrate side-chains, since non-glycosylated, single and two-chain UK are also incorporated.

Incorporation also appears to be somewhat species specific, in that rabbit platelets do not incorporate any type of pro-UK, whereas dog platelets, which contain a significant amount of endogenous dog pro-UK, incorporate human pro-UK in vitro, and in vivo after bolus injection (e.g. 0.5 mg/kg).

Thus, according to the invention, the platelet, and in particular, the platelet membrane, serves as a carrier to transport the u-PA, e.g., pro-UK, to the site of a platelet-mediated forming thrombus. This "intra-platelet membrane" pro-UK is subsequently activated locally and serves as a potent inhibitor of thrombotic occlusions, especially in arteries where thrombosis is known to be platelet-mediated and thrombi are platelet-rich (commonly called white thrombi). Moreover, since platelets do not inhibit pro-UK activity, this plasminogen activator is especially effective against platelet-rich thrombi, whereas platelets are known to block the activity of other activators, e.g., t-PA or SK, due to the platelets' rich content of inhibitors, i.e., α-2 antiplasmin and plasminogen activator inhibitor-1. Thus, the pro-UK-loaded platelets accumulate wherever a new blood clot is about to form, and there allow the pro-UK to exert its local anti-thrombotic effect, which is resistant to inhibitors, to prevent occlusive thrombus formation.

In general, the invention features a method of adjunctive therapy to inhibit reocclusion in a patient after thrombolytic treatment, by administering to the patient a bolus of an amount of purified pro-urokinase ("pro-UK") that inhibits the formation of occlusive thrombi without inducing a systemic effect in the patient, e.g., 5 to 40 mg, the amount of pro-UK is administered after the completion of the thrombolytic treatment and periodically, e.g., once every 1 to 10 days, thereafter for the period of risk of reocclusion, wherein the pro-UK becomes incorporated by platelets of the patient for subsequent activation during thrombosis to inhibit reocclusion in the patient.

Since the $T_{1/2}$ of pro-UK in plasma is about 7 minutes, only the intra-platelet pro-UK will be operative under these conditions.

The term "rethrombosis" includes any formation of a new thrombus after any form of thrombolysis, e.g., with UK, t-PA, SK, or high dosage pro-UK, to remove thrombi. The term "reocclusion" includes any rethrombosis and restenosis, and any other form of closure of a blood vessel mediated by platelets, that occurs after any form of thrombolytic treatment, e.g., thrombolysis and angioplasty. As used herein, the term "occlusive thrombus" means any thrombus that partially or completely occludes a blood vessel.

The period of risk of reocclusion after thrombolytic treatment is typically about 3 months. In the first 48 hours after treatment, the risk is between 5 and 30 percent. From 48 hours to three months, the risk is an additional 30 percent, i.e., a vessel that is open after 48 hours still has a 30% chance of reocclusion within the next three months.

Administration involves either an intravenous or subcutaneous bolus, e.g., 5 to 40 mg, depending on the threshold level of pro-UK that will induce a systemic effect in a particular patient, once every 1 to 10, or 1 to 5 days for the risk period. The latter is suitable for self-administration over long periods. The pro-UK may be recombinantly produced, and/or may be a thrombin-resistant mutant form of pro-UK, e.g., containing a mutation at amino acid locations 135, 156, or 157. In a preferred embodiment, the pro-UK is administered after thrombolytic treatment by daily intravenous bolus injections of 5 to 30 mg for 1 to 2 weeks, followed by subcutaneous injections of 5 to 30 mg every 1 to 5 days for at least 3 months.

The invention also features a method of inhibiting the formation of platelet-mediated thrombi in a clot-free patient, by periodically, e.g., once every 1 to 10 days, administering to the patient a bolus of an amount of purified pro-UK, e.g., pro-UK or thrombin-resistant mutant pro-UK, that inhibits the formation of occlusive thrombi without inducing a systemic effect in the patient, wherein the pro-UK becomes incorporated by platelets of the patient for subsequent activation during thrombosis to inhibit platelet-mediated thrombosis. Administration can be by an intravenous or subcutaneous injection of a bolus of, e.g., 5 to 40 mg, once every 1 to 5 days.

The term "clot-free", as used herein to define a patient, means a person who has no clinical evidence of intravascular thrombosis, e.g., a person who is not in the acute clinical phase of an illness caused by an occlusive thrombus in any of these major blood vessels. The acute clinical phase usually lasts about 5 to 7 days after a thrombus occludes a vessel. The term also includes a patient who has undergone successful thrombolytic treatment, e.g., the administration of a thrombolytic agent such as tPA, UK, pro-UK in high doses, or SK, or angioplasty, to clear the vascular system of occlusions.

In addition, the invention features a method of prophylactic treatment against cardiovascular disease, e.g., atherosclerosis, in a patient, by administering to the patient a bolus of an amount of purified pro-UK that inhibits platelet-mediated fibrin deposition without inducing a systemic effect in the patient, the amount of pro-UK is administered once or twice weekly, wherein the pro-UK becomes incorporated by platelets of the patient for subsequent activation during thrombosis to inhibit platelet-mediated fibrin deposition and resultant cardiovascular disease.

The invention also features a method of prolonged thrombolytic therapy with pro-UK in a patient by enriching the content of pro-UK in the platelets of the patient, by administering to the patient a thrombolytic dosage of purified pro-UK and thereafter administering a bolus of a supplemental dosage of pro-UK in an amount that lyses existing thrombi and inhibits the formation of new occlusive thrombi without inducing a systemic effect in the patient, the supplemental dosage of pro-UK is administered at periodic intervals for the duration of therapy, wherein the pro-UK is incorporated by the platelets of the patient and extends the effective half-life of the thrombolytic effect of pro-UK, by a factor of about 1000-fold.

As used herein, the term "increasing the effective half-life of pro-UK" covers raising the half-life of pro-UK in plasma, which is about 7 to 8 minutes, to the effective "half-life" of the platelets in the bloodstream, which is about 4 to 5 days.

In preferred embodiments, the thrombolytic dosage of pro-UK is infused at a dosage of up to about 80 mg/hour, and the supplemental dosage of pro-UK is administered subcutaneously or intravenously in a bolus of 5 to 40 mg. The supplemental dosage of pro-UK may be administered once every 1 to 5 days and starting within 1 to 3 days after the thrombolytic administration.

The invention also features a method of long-term inhibition of thrombosis in a patient, by periodically administering to the patient a bolus of purified pro-UK in an amount that inhibits thrombosis without inducing a systemic effect in the patient, e.g., 5 to 40 mg, below that which would induce a systemic effect in the patient, wherein the pro-UK becomes incorporated by the platelets of the patient and remains there for the intravascular life of the intact platelet. For example, the pro-UK may be administered once every 2 to 5 days for a period of at least 3 months.

The invention also features a method of treating transient arterial insufficiency in a patient, by administering a bolus of purified pro-UK to the patient in an amount that inhibits the formation of occlusive thrombi without inducing a systemic effect in the patient, the amount of pro-UK is administered daily during symptomatic periods, e.g., during periods of neurological symptoms or pain caused by arterial insufficiency, and once every 1 to 3 days thereafter until the arterial insufficiency is stabilized. The transient arterial insufficiency may be in the heart and cause unstable angina pectoris, or may be in the brain and cause transient ischemic attacks.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

Applicant's finding suggests that there are two intravascular compartments in which u-PA, e.g., pro-UK, is found, an extra-platelet or plasma compartment, and an intra-platelet membrane compartment. Pro-UK incorporated into young platelets has a $T_{1/2}$ which is about 1,000-fold longer than pro-UK in plasma. As a result, the pro-UK administered to a patient that becomes incorporated into the platelets gains an exceptionally long duration of action which cannot be approximated by any other known method. Moreover, the anti-thrombotic action of intra-platelet pro-UK is greatly enhanced compared to that of endogenous pro-UK in plasma, because this form of pro-UK is concentrated directly in forming blood clots, which provides a substantially localized and specific effect.

Experimental Studies

Applicant has conducted various in vitro and animal studies to determine the specificity, effective half-life, and anti-thrombotic effect of the newly discovered intra-platelet membrane u-PA. Native pro-UK purified from the culture medium of a human kidney tumor cell was obtained from Collaborative Research Inc. (Bedford, Mass.). Recombinant pro-UK (rec-pro-UK) from *E. coli* was obtained from Farmitalia Carlo Erba (Milan, Italy). LMW-UK was obtained from Abbott Laboratories (Chicago, Ill.).

Preparation of Platelets

Human platelets were prepared from venous blood added to 3.8% citrate (9: 1). Platelet-rich plasma ("PRP") was obtained by centrifuging this blood-citrate mixture at 160 g for 15 minutes at room temperature. Platelet-poor plasma ("PPP") was obtained by adding prostaglandin $E_1$ ("$PGE_1$") (1 μM) to the PRP, centrifuging this mixture at 725×g, and removing the PPP. The platelets were resuspended by gentle mixing in HEPES Tyrodes-albumin buffer ("HTA") containing 128 nM NaCl, 8.9 mM $NaHCO_3$, 5.6 mM dextrose, 10 mM HEPES 0.35 mg/ml BSA, 12 mM KCl, 3 mM KCl, 3 mM $KH_2PO_4$, and 3 mM $MgCl_2$, with a pH of 7.5. The washing was repeated twice, and the supernatant removed after centrifugation each time. Platelet counts were determined in a Coulter counter (Coulter Electronics, Hialeah, Fla.).

Endogenous U-PA in Platelets

Figure 1:
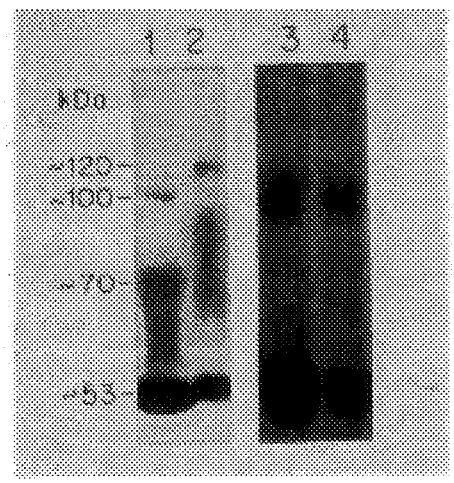
FIG. 1 is a zymogram of washed platelets and platelet-poor plasma with added pro-UK, with and without acid washing.

FIG. 1 is a zymogram which shows the endogenous u-PA intrinsic to platelets and plasma. Lane 1 shows platelets ($1 \times 10^8$) washed once in HTA buffer with a dominant plasminogen activator band of activity at ~53 kDa corresponding to u-PA. In addition, a band at ~70 kDa corresponds to tPA, which has previously been shown to bind to platelets by a specific, low affinity binding site. Vaughan et al., *J. Biol. Chem.*, 264: 15869–74 (1989). In addition, a ~100 kDa band was seen in the platelets, consistent with a UK: plasminogen activator inhibitor-1 ("PAI-1") complex. Lane 2 shows the corresponding PPP, which also showed a band of u-PA activity, and a 120 kDa band consistent with a tPA: PAI-1 complex. The UK: PAI-1 complex was invariably absent in the PPP (lane 2).

From the zymograms (not shown) of PPP (1–20 µl) and platelets ($10^7$–$10^8$), it was estimated the about 20% of the u-PA in blood was present in platelets based on their zymographic activities. The final wash (20 µl HTA buffer) was invariably devoid of activity, indicating that the buffer remaining with the platelet pellet was not the source of the zymographic activity.

Loading Platelets with U-PA, TPA or Streptokinase

To determine whether the platelets incorporate pro-UK, UK, tPA, or streptokinase, washed platelets were incubated (37° C.) in PPP or HTA buffer ($4 \times 10^8$ platelets/ml), enriched with 0.5 g/ml of native pro-UK or rec-pro-UK, HMW-UK, LMW-UK (which is missing most of the A chain), tPA, or streptokinase for 5 minutes. The two UK preparations, tPA, and streptokinase were incubated only in the buffer to avoid complexation with inhibitors naturally found in plasma. Thereafter, the platelets were recovered by centrifugation (725×g for 15 min.), washed twice in HTA buffer, resuspended in bank plasma, and reincubated for 0.5, 1, 2 and 22 hours. At the end of the final incubation period, the platelets were recovered by centrifugation, washed twice in HTA buffer and examined by zymography on plasminogen enriched casein plates. The corresponding PPP (20 µl) at the end of each incubation period was examined alongside the platelets. These tests showed that only high molecular weight pro-UK and UK, having a MW of about 53 kDa, is incorporated.

Figure 2:
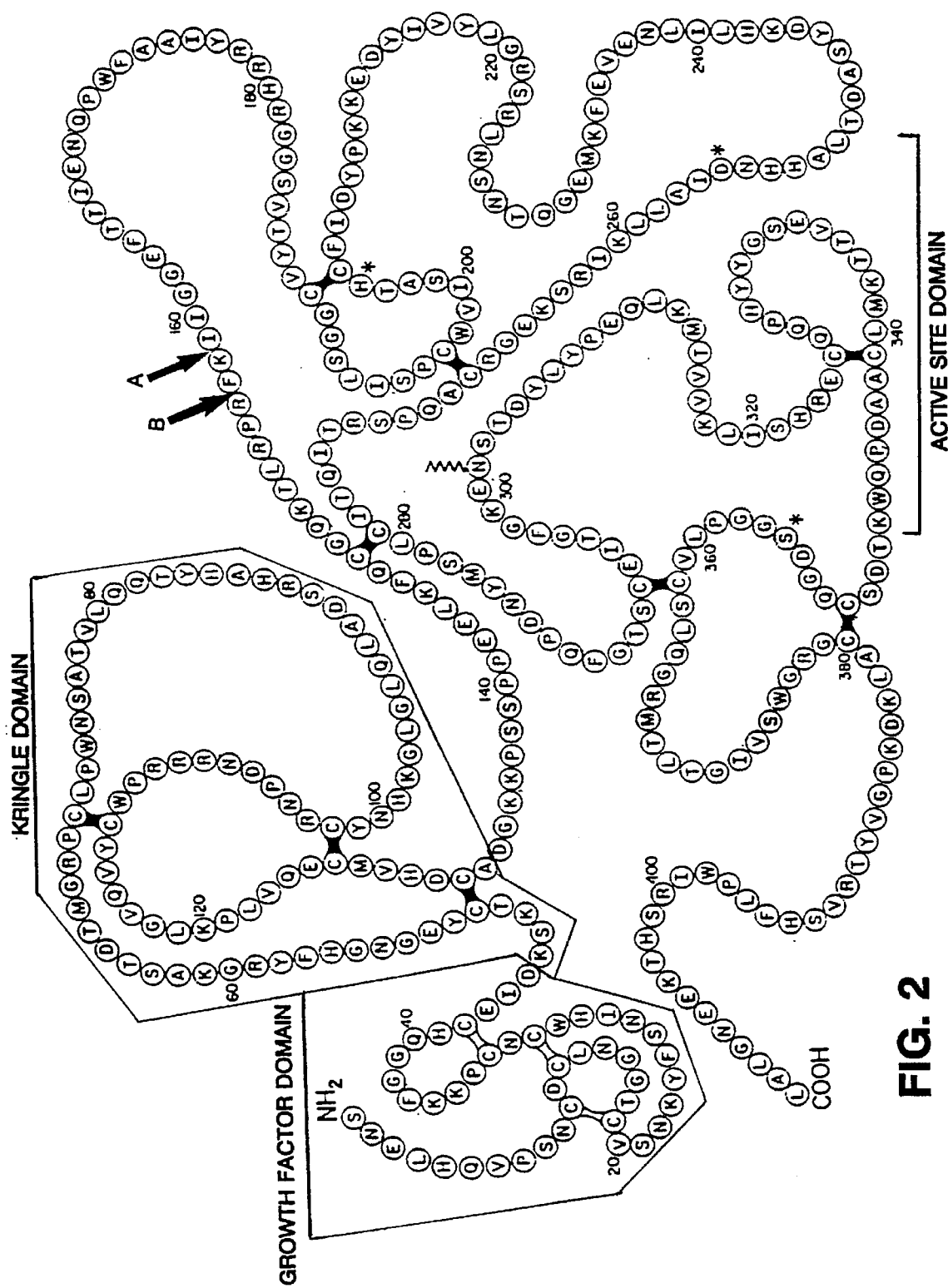
FIG. 2 is a schematic representation of the primary amino acid sequence of single chain pro-UK (SEQ ID NO: 1).

Thus, the incorporation of u-PA into the platelet membrane is specific for HMW (53 kDa) u-PA, either native glycosylated or recombinant unglycosylated, and either the single-chain proenzyme (pro-UK) or the two-chain enzyme (HMW-UK). No incorporation was found with LMW (33 kDa) u-PA (which lacks the A-chain), tissue plasminogen activator (t-PA), or streptokinase. This confirms the finding that incorporation is dependent on the A-chain of u-PA, which bears the growth factor and kringle domains (shown in FIG. 2, SEQ ID NO: 1), but not the catalytic site of u-PA. The two arrows in FIG. 2 indicate the plasmin cleavage (activation) site ($Lys^{158}$-$Ile^{159}$) and the thrombin cleavage site ($Arg^{155}$-$Phe^{156}$) in the primary amino acid sequence of single chain u-PA (pro-UK).

Acid Washing of Platelets

Platelets loaded with pro-UK were washed in acid to determine whether intra-platelet membrane pro-UK could be dissociated from the platelets. A pellet of ~$1 \times 10^8$ washed platelets loaded with pro-UK as described above was resuspended in 1.0 ml of 20 mM citrate (pH 4.5), 0.15 M NaCl, and 0.3 mg/ml BSA. After 5 min., the platelets were spun down and resuspended in 10 ml of HTA buffer. After an additional 5 min., the platelet pellet was recovered by centrifugation and then analyzed by zymography. Acid washing by this procedure was shown to completely remove platelet-bound tPA and prekallikrein, but not intra-platelet pro-UK.

As shown in FIG. 1, when platelets preincubated with native pro-UK (0.5 µg/ml) in PPP for 5 min. were washed twice in HTA buffer, the tPA band seen in lane 2 is no longer seen in lane 3. The increased density of the bands in lanes 3 and 4 was due to additional pro-UK in the platelets as a result of the preincubation. Subsequent acid washing of the platelets induced only slight reduction in the intensity of the u-PA or u-PA: PAI-I complex, and did not significantly dissociate the pro-UK (lane 4).

Figure 3:
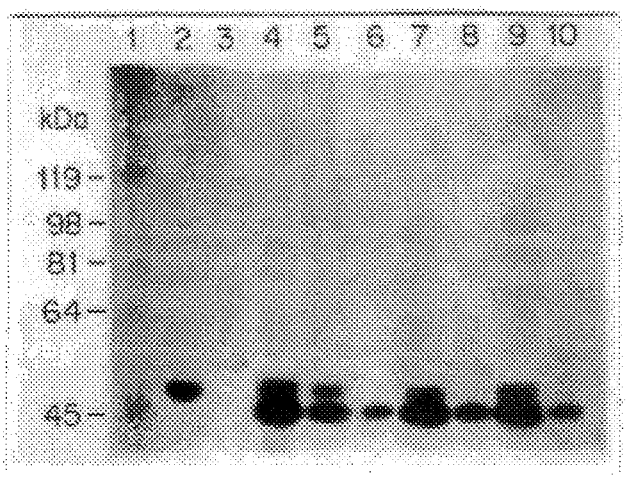
FIG. 3 is a zymogram of washed platelets and platelet-poor plasma incubated with recombinant pro-UK (rec-pro-UK).

As shown in FIG. 3, the uptake of pro-UK from the ambient fluid was most apparent when rec-pro-UK was used, since it was clearly resolved migrating ahead of the endogenous pro-UK. Rec-pro-UK is non-glycosylated, i.e., has no carbohydrate side-chains, and therefore has a lower molecular weight than endogenous pro-UK, which leads to its faster migration in SDS-PAGE gels. The control platelet preparation is shown in lane 2 alongside the control PPP in lane 3. The PPP induced no lysis bands due to the relatively short (14 hour) incubation time of the plate, since the amount of pro-UK in the PPP sample was less than in the platelets. The higher MW lysis zone from the endogenous pro-UK intrinsic to platelets was similar in all the lanes indicating no significant differences in the number of platelets in each sample, and that the endogenous pro-UK in platelets was not dissociated by the incubations in PPP for up to 22 hours. The platelets incubated with rec-pro-UK and then washed and reincubated in normal, unenriched PPP for 30 minutes (lane 4), 1 hour (lane 5), 2 hours (lane 7) and 22 hours (lane 9) induced comparable lysis zones, indicating no apparent dissociation of the rec-pro-UK over this time period. Lane 1 shows molecular weight markers.

FIG. 3 also shows a small but unchanging amount of rec-u-PA activity in the corresponding PPP at the end of each incubation period (lanes 6, 8, and 10) indicating that a fraction of the rec-pro-UK was released within the first 30 minutes, probably representing the unincorporated portion. However, the bulk of the intra-platelet rec-pro-UK remained unaffected by the incubation, regardless of the length of the incubation period, consistent with incorporation into the platelets. Moreover, this portion of the rec-pro-UK also resisted dissociation by acid washing as shown for native pro-UK in FIG. 1.

Incubation of platelets with native HMW-UK in HTA buffer induced similar uptake of the UK. Uptake of UK was not accompanied by any more inhibitor complex formation than that seen with pro-UK, suggesting that storage of u-PA in platelets is separate from that of PAI-1, or that most of the latter is in a latent form. By contrast, incubation with LMW-UK or tPA in HTA buffer at the same concentrations induced no uptake by platelets.

Both endogenous pro-UK intrinsic to platelets, and exogenous pro-UK, were incorporated by platelets, as evidenced by a resistance to dissociation by acid washing or by prolonged (22 h) incubation in a pro-UK-poor environment. Platelets contain an estimated 20% of the pro-UK present in the blood of healthy subjects.

Pro-UK is Incorporated Into Platelet Membranes

Pro-UK was labelled with $^{125}I$ via a lactoperoxidase reaction using Enzymobeads (BioRad Laboratories, Richmond, Calif.) and incubated with platelets to determine whether the pro-UK was bound to the open canalicular system (OCS) of the platelet membrane. Autoradiography electron microscopy of these platelets gave identical images before and after osmotic swelling of the platelets in distilled water, which obliterates the OCS, indicating that the pro-UK was not merely bound to the surface canaliculae, but was incorporated or internalized into the platelet.

Platelets were then broken up by three 10 minute sonications followed by centrifugation at 10,000 g for 10 minutes. The platelet membranes were then separated from the supernatant by centrifugation at 100,000 g for about 10 minutes. All of the endogenous and the exogenous pro-UK was found by zymography to be firmly associated with the membrane, which indicated that the pro-UK was incorporated into the platelet membrane.

Incorporation of u-PA into the platelet membrane is dose dependent, not reversible by acid washing, and difficult to saturate, indicating that incorporation into the membrane is not mediated by any known receptor. Although a platelet-receptor for the 53 kDa u-PA has previously been reported by Vaughan et al., *Fibrinolysis*, 4: 141–146 (1990), this alleged receptor is not involved in the membrane uptake of u-PA described because incorporation was blocked by low pH or high salt, and these same buffer conditions failed to remove u-PA once it was incorporated into the platelet membrane. In fact, no method for removing the membrane-bound u-PA has been found. Furthermore, a 50 to 100-fold excess of unlabeled pro-UK did not inhibit incorporation of radiolabeled u-PA into platelets.

Figure 4A:
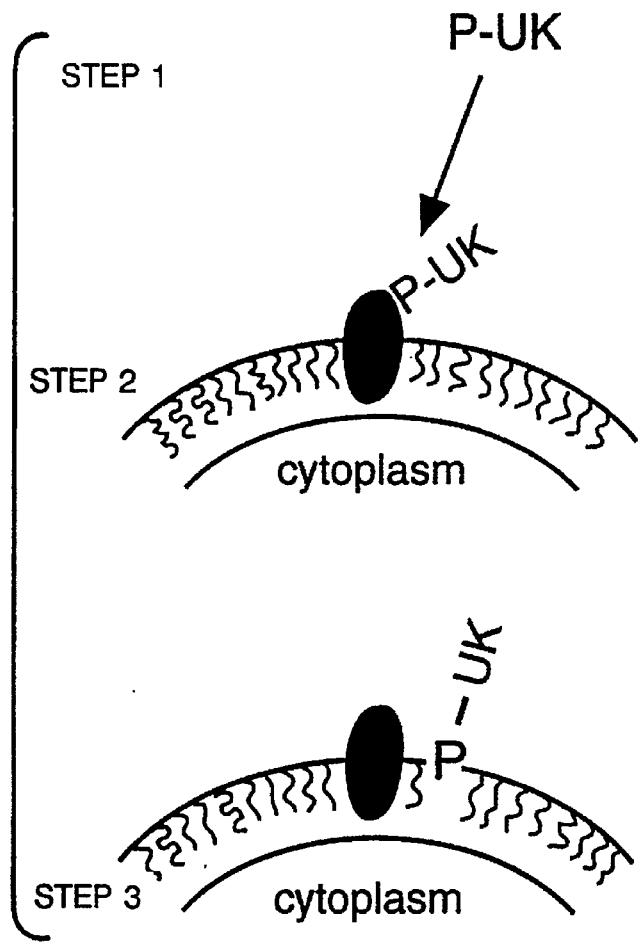
FIG. 4A is a schematic of the proposed two-step mechanism for u-PA incorporation into platelet membranes.

Based on these results, a two-step incorporation mechanism is postulated. In the first step, u-PA binds transiently with a platelet membrane protein yet to be identified in a high-affinity interaction that leads to a conformational change in the u-PA that exposes a hydrophobic region of the A-chain. In the second step, this hydrophobic region of the A-chain of u-PA is introduced into the plasma membrane lipid layer resulting in rapid intercalation of this A-chain region into the lipid layer of the membrane. At the same time, the catalytic domain on the u-PA B-chain remains outside of the platelet membrane, because the plasminogen activation activity of platelet membrane-bound u-PA is unimpaired. This pathway is illustrated schematically in FIG. 4A.

Figure 4B:
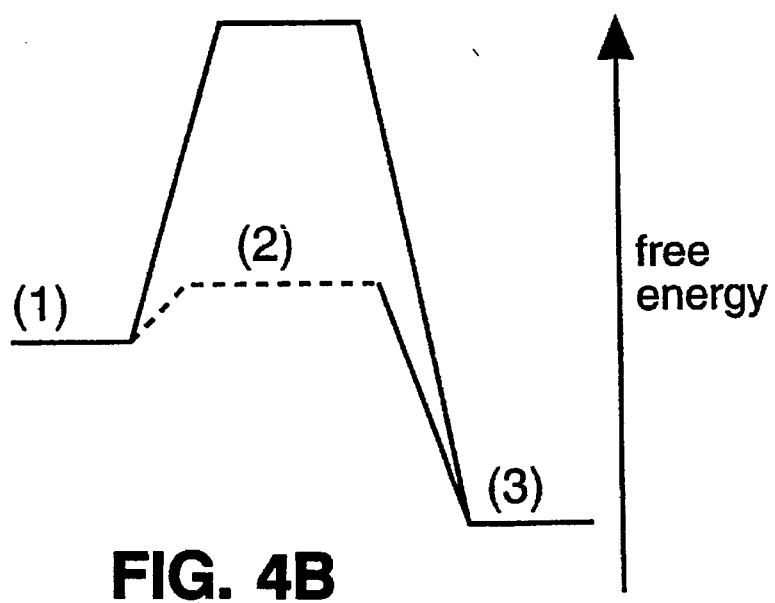
FIG. 4B is a graphical representation of the free energy of the mechanism of FIG. 4A.

The incorporation of u-PA into the platelet membrane is energy independent in that it is not inhibited by cold temperature (4° C.) or by a wide spectrum of metabolic or other inhibitors (cytochalasin B at 30 μg/ml, colchicine at 20 μM, procaine at 0.4%, dinitrophenol at 5 mM, azide at 0.1%, Na cyanide at 5 mM, EDTA at 5 mM, DMSO at 3.0%, $PGE_1$ at 1.0 μM). FIG. 4B graphically illustrates the direction of free energy in the pathway depicted in FIG. 4A.

Figure 5:
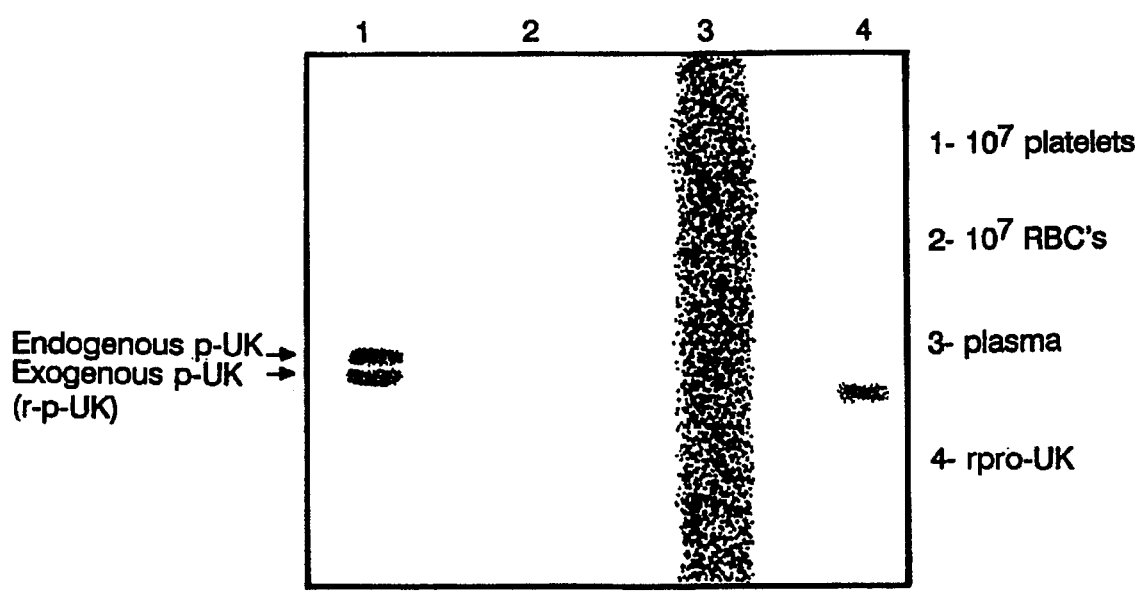
FIG. 5 is a zymogram showing endogenous and rec-pro-UK incorporated into platelets but not red blood cells from the same blood.

Furthermore, the phenomenon of membrane incorporation of u-PA is selective for platelets, since equivalent incorporation could not be demonstrated in human red cells, monocytes, or endothelial cells using the same incubation conditions described above. For example, this selectivity was demonstrated by experiments in which pro-UK was incubated in citrated whole blood followed by isolation of the red cells and platelets. Despite the 1,000-fold greater number and greater surface area of red blood cells, all the detectable pro-UK was found in the platelets. This is illustrated by the zymogram of FIG. 5, which shows endogenous and rec-pro-UK in the platelets, but not in the red cells from the same blood. Lane 1 shows $10^7$ platelets, lane 2 shows $10^7$ red blood cells, lane 3 shows plasma, and lane 4 shows rec-pro-UK.

Figure 6:
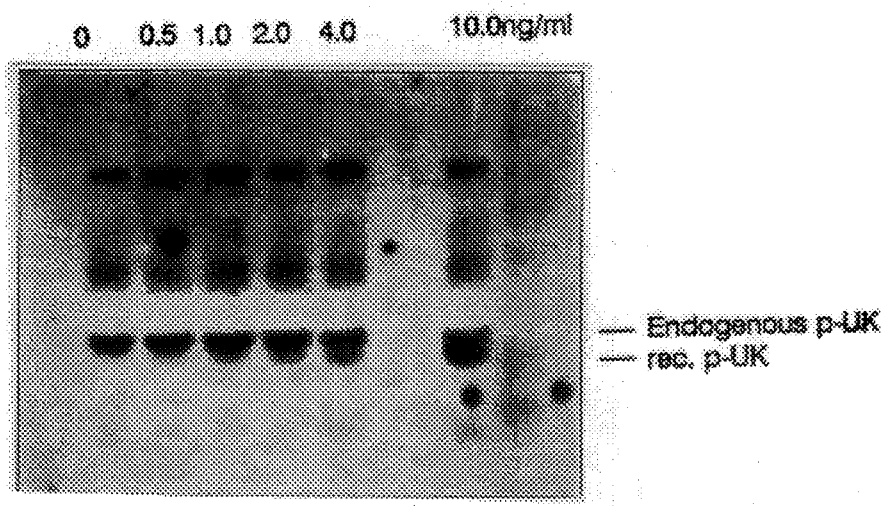
FIG. 6 is a zymogram showing platelets isolated from whole blood incubated for 30 minutes with 0 to 10 ng/ml rec-pro-UK.

Platelet uptake of pro-UK in whole blood also was found to be sensitive to very small concentrations of pro-UK. For example, when citrated whole blood was incubated with 0.5 to 10 ng/ml of rec-pro-UK for 30 minutes, zymographically detectable quantities were taken up at a concentration of $\geq 0.5$ ng/ml. Rec-pro-UK from *E. coli* was used in these experiments because it is non-glycosylated and therefore migrates ahead of the endogenous native pro-UK on SDS gel electrophoresis. At a concentration of about 4 ng/ml, about 20% of this amount was incorporated into the platelets, which is about the same percentage of endogenous pro-UK found in platelets in normal human blood. This is illustrated by the zymogram shown in FIG. 6, which shows platelets isolated from whole blood incubated for 30 minutes with 0, 0.5, 1.0, 2.0, 4.0, and 10 ng/ml rec-pro-UK (lanes 1 through 6, respectively).

Animal Studies

Human rec-pro-UK (0.5 mg/kg bolus) was administered i.v. over one minute into dogs and allowed to mix in the blood with dog platelets to determine whether human pro-UK is incorporated into these dog platelets. Blood samples were collected at 0 min., 15 min., 30 min., 1 hour, and 2 hours. The pro-UK in the platelets and plasma was analyzed by casein autography as described in Vassalli et al., *J. Exp. Med.*, 159: 1653–1668 (1984), which is incorporated herein by reference. Considerable uptake of rec-pro-UK was seen in the dogs, and the amount of pro-UK shown to be incorporated in a sample taken at 15 minutes after injection of the pro-UK did not change over the two hour period of observation, i.e., there was about the same amount of pro-UK in the platelets in the 2 hour sample as in the 15 minute sample. No rec-pro-UK was detectable in the plasma samples after 30 minutes due to the rapid clearance of pro-UK from plasma.

Applicant has also discovered that under similar conditions, rabbit platelets do not incorporate human pro-UK. A 0.5 mg/kg bolus of pro-UK was injected intravenously into rabbits, and the plasma and platelets were tested at 0 min., 15 min., 30 min., and hourly thereafter for 5 hours. None of the human rec-pro-UK was incorporated into the rabbit platelets. Applicant also found that rabbit platelets do not appear to contain any endogenous rabbit pro-UK, whereas dog platelets contain substantial amounts of dog pro-UK.

Prophylactic Administration

Since the intra-platelet u-PA, e.g., pro-UK, has a lifetime in the plasma equal to that of its platelet carrier, it will last 4 to 5 days on average, depending upon the age of the particular platelet by which it was incorporated. To keep the platelet compartment maximally loaded with pro-UK to achieve the long-term prophylactic effect according to the invention, u-PA such as pro-UK is preferably administered once every 1 to 3 days in a single bolus of a small amount that will not induce a systemic effect, e.g., about 5 to about 40 mg, depending on the particular patient.

The upper dosage limit depends on a number of factors that can be used to estimate a threshold level of pro-UK in the blood above which systemic effects will occur in a specific patient. The pro-UK dosage must be kept below this level. This threshold is higher in patients with greater weight and/or a higher PAI-1 level, and is monitored by measuring the levels of plasminogen, fibrinogen, and fibrinogen degradation products in the blood.

This threshold is determined as follows. First, the baseline blood levels of plasminogen and fibrinogen are measured for each patient using standard techniques. In addition, the blood is tested for fibrinogen degradation products, to confirm that there are none. A dosage of pro-UK of about 0.3 to 0.4 mg/kg (about 20–30 mg for a 70 kg patient) is then administered, and the patient's blood levels of plasminogen, fibrinogen, and fibrinogen degradation products are monitored. The pro-UK dosage is too high if a systemic effect is observed, i.e., the baseline levels of plasminogen or fibrinogen are depleted by 20% or more, or if the concentration of fibrinogen degradation products rises above about 100 mg/ml of blood. If the initial dose is too high, a somewhat lower dosage, e.g., about 5 mg less than the first dose, is administered the next day, and the blood levels are again monitored. If the first dose of pro-UK does not induce a systemic effect, a somewhat higher dosage may be administered the next day. In this way, the desired dosage, i.e., the highest dosage of pro-UK that does not induce a systemic effect, for a specific patient can be determined within one or two days. This dosage is then used for continued periodic therapy as required. Subcutaneous administration gives varying absorption rates, and can therefore be carried out with somewhat higher dosages.

The pro-UK is administered to a patient, e.g., following thrombolytic therapy, as a bolus of native or recombinant, single-chain, high molecular weight (about 50 kDa) pro-UK or mutant pro-UK. This bolus may be injected intravenously at intervals ranging from daily to once every 2 to 4 days, depending on the indication. Longer intervals between injections, e.g., 5 to 10 days, may be used, but the effectiveness of such administration decreases as the interval between administrations increases.

Alternatively, the bolus may also be injected subcutaneously once every 1 to 3 days, and preferably daily, which provides the long-term prophylaxis according to the invention, and the added benefit of self-administration.

Prevention of Reocclusion Following Thrombolytic Therapy

Reocclusion often occurs within hours after successful lysis of a thrombus with tPA, SK, and other thrombolytic agents, and substantially attenuate the therapeutic effect of these agents. Attempts have been made to prevent such reocclusion by the administration of heparin; however, heparin has been shown to be relatively ineffective to prevent reocclusions following coronary thrombolysis, and a number of new agents are being tested to deal with this problem. However, all these agents induce a systemic effect which is associated with an increased risk of bleeding.

To prevent the undesired reocclusion associated with these thrombolytic agents, a bolus of 5 to 40 mg of pro-UK is administered intravenously immediately, or within a few hours or a day, after the completion of thrombolytic therapy, and additional boluses of the same dosage are administered intravenously thereafter once daily throughout hospitalization, which is typically about 10 days. Thereafter, subcutaneous or intravenous injections of a similar dosage every 1 to 3 days are administered during the "risk period," which is about three months after thrombolysis, since it is known that there is about a 30% reocclusion rate in the first three months after coronary thrombolysis. As described above, the dosage of pro-UK is an amount which effectively inhibits thrombus formation, but does not cause a systemic effect.

The thrombolytic effect of tPA ends once infusion of the agent is completed, and the risk of reocclusion is the highest with tPA compared with other thrombolytic agents. Therefore, when tPA is used as the thrombolytic agent, according to the invention pro-UK should be administered to the patient immediately after the tPA infusion is finished.

When SK is used as the thrombolytic agent, major systemic effects arise, which have an anti-thrombotic effect for a few hours after the thrombolytic therapy is completed. Therefore, pro-UK may be administered at any time within several hours after the completion of SK therapy.

Due to the incorporation of pro-UK into the platelets in the bloodstream, thrombolysis using pro-UK as the thrombolytic agent is associated with a low rate of reocclusion (1–5%) for at least the first 24 hours. When pro-UK is used as a thrombolytic agent, it is typically infused to lyse clots at a high dosage of, e.g., 80 mg/hour. Thereafter, supplemental administrations of low dosages of pro-UK, e.g., at 1 to 3 day intervals, starting 1 to 3 days after the initial administration is complete, are preferably given according to the present invention to prolong the thrombolytic effect of the pro-UK. These low, supplemental dosages of pro-UK are fibrin specific, and therefore do not give rise to a systemic effect. As a result, this form of prolonged thrombolytic therapy will be accompanied by a lower incidence of hemorrhagic side effects then traditional anti-thrombotic agents, e.g., heparin, anti-thrombins, and anti-platelet agents.

In addition, the use of optimal doses of anti-platelet agents, such as heparin, hirudin, and aspirin, during thrombolytic therapy with any thrombolytic agent does not pose a contra-indication to the use of pro-UK according to the invention.

Prevention of Reocclusion Following PTCA

A principal limitation of PTCA for coronary artery stenoses is that about 30% of these lesions reocclude within three months. Although the pathophysiology of restenosis is not completely understood, it is generally believed to be mediated at least in part by platelets. No effective therapy or prevention has been established.

According to the invention, this incidence of reocclusion is reduced by the administration of a bolus of 5 to 30 or 40 mg pro-UK injected intravenously immediately to within one day after completion of angioplasty, followed by subcutaneous injections of the same dosage boluses once every 1 to 3 days for at least 3 months. Since pro-UK is a zymogen, it is essentially inert in blood at these dosages, and is therefore essentially free of undesirable side-effects such as systemic fibrinolysis or bleeding.

Treatment of Transient Arterial Insufficiency

Transient arterial insufficiency occurs when a diseased blood vessel is partially or completely occluded by the presence of fibrin and platelets at a site of damage in the vessel. Such an insufficiency in the brain results in so-called transient ischemic attacks, and in the heart results in unstable angina pectoris. Although such an occlusion may be temporary, it is typically associated with symptoms such as neurological symptoms in transient ischemic attacks, and sharp pain in unstable angina. Transient ischemic attacks may also give rise to a stroke. Unstable angina pectoris, which is often due to "sputtering" coronary thrombosis, may herald an impending heart attack.

Thrombolytic therapy with available agents has not met with much success for these indications, because of their short duration of action, prothrombotic effects, and hemorrhagic complications with prolonged administration. By contrast, bolus intravenous, or alternatively subcutaneous, daily injections of pro-UK, in an amount below that which would cause a systemic effect, during periods of ischemia and associated symptoms, and once every 1 to 3 days thereafter at the same dosage level until the arterial insufficiency has stabilized, should be very effective due to the incorporation of pro-UK by platelets, which are generally believed to have a significant role in these transient arterial insufficiencies.

Prophylaxis of Cardiovascular Disease

Atherosclerosis and thrombosis in the arterial circulation are believed, in large part, to be platelet-mediated. According to the invention, intravenous or subcutaneous injections of an amount of purified pro-UK that inhibits platelet-mediated fibrin deposition without inducing a systemic effect in the patient, e.g., 1 to 40 mg of pro-UK, at regular intervals, e.g., every 3 to 10 days, should be a safe and effective prophylactic treatment for cardiovascular disease. Cardiovascular disease includes coronary disease such as angina, cerebral vascular disease such as transient ischemic attacks, and peripheral vascular disease such as peripheral arterial occlusions.

Thrombin-Resistant Pro-UK Mutants

Mutant forms of pro-UK, e.g., Arg-156 and Asp-157 mutants, which resist inactivation by thrombin, are known in this field, though to date they have not found a place in therapy. For example, pro-UK mutants resistant to plasmin and/or thrombin (e.g., Phe-157 to Asp, and Lys-135 to Gln and Phe-157 to Asp) have been constructed by site-directed mutagenesis with the aim of producing more efficient thrombolytic agents, e.g., as described in Miyake, T. et al., *J. Biochem. (Tokyo)*, 104: 643–647 (1988), which is incorporated herein by reference. Recombinant mutant pro-UKs have also been expressed in *E. coli* as described in Eguchi et al., *J. Biochem. (Tokyo)*, 108: 72–79 (1990), which is incorporated herein by reference. Similarly, Arg-156 pro-UK mutants can be made by site-directed mutagenesis to produce the preferred thrombin-resistant pro-UK mutants.

In the presence of thrombin, these pro-UK mutants show efficient clot lysis, compared with wild type and rec-pro-UK. In the absence of thrombin, when measured by a fibrin plate method in a purified system, these mutants typically have lower specific activities than wild type or rec-pro-UK, because their catalytic constants for conversion to the two-chain form (UK) by plasmin are lower. However, when tested in plasma, the Gln-135/Asp-157 mutant lysed clots as efficiently as rec-pro-UK by retaining the single-chain form, whereas the rec-pro-UK was partially converted to the two-chain form.

Since a forming platelet-mediated thrombus is especially rich in thrombin, which is known to inactivate pro-UK (Gurewich et al., *Blood*, 69: 769–772 (1987)), a thrombin-resistant mutant pro-UK that becomes incorporated into platelets may be especially well suited for the above described novel applications of pro-UK and may be substituted for pro-UK in all the indications listed.

Other Embodiments

Other embodiments are in the following claims.

What is claimed is:

1. A method of adjunctive therapy to inhibit reocclusion in a patient after thrombolytic treatment, said method comprising administering to the patient a bolus of an amount of purified pro-urokinase ("pro-UK"), said amount of pro-UK is administered after the completion of the thrombolytic treatment and once every 1 to 10 days thereafter for the period of risk of reocclusion, wherein said pro-UK becomes incorporated by platelets of the patient for subsequent activation during thrombosis to inhibit reocclusion in the patient.

2. The method of claim 1, wherein said pro-UK is recombinantly produced.

3. The method of claim 1, wherein said pro-UK is a thrombin-resistant mutant form of pro-UK.

4. The method of claim 1, wherein said pro-UK is administered intravenously or subcutaneously in a bolus of 5 to 40 mg once every 1 to 5 days.

5. The method of claim 4, wherein said pro-UK is administered after thrombolytic treatment by daily intravenous bolus injections of 5 to 40 mg for 1 to 2 weeks, followed by subcutaneous injections of 5 to 40 mg every 1 to 5 days for at least 3 months.

6. A method of preventing occlusion in a clot-free patient, said method comprising administering to the patient once every 1 to 10 days a bolus of an amount of purified pro-UK, wherein said pro-UK becomes incorporated by platelets of the patient for subsequent activation during thrombosis to inhibit platelet-mediated thrombosis.

7. The method of claim 6, wherein said pro-UK is administered intravenously or subcutaneously in a bolus of 5 to 40 mg once every 1 to 5 days.

8. A method of prolonged thrombolytic therapy with pro-UK in a patient by enriching the content of pro-UK in the platelets of the patient, said method comprising administering to the patient a thrombolytic dosage of purified pro-UK and thereafter administering a bolus of a supplemental dosage of pro-UK in an amount that lyses existing and forming thrombi, said supplemental dosage of pro-UK is administered once every 1 to 10 days for the duration of therapy, wherein said pro-UK is incorporated by the platelets of the patient which extends the normal effective half-life of the thrombolytic effect of pro-UK.

9. The method of claim 8, wherein said thrombolytic dosage of pro-UK is infused at a dosage of up to about 80 mg/hour.

10. The method of claim 9, wherein said supplemental dosage of pro-UK is a bolus of 5 to 40 mg.

11. The method of claim 8, wherein said supplemental dosage of pro-UK is administered once every 1 to 5 days and starting within 1 to 3 days after the thrombolytic administration.

12. A method of long-term treatment of thrombosis in a patient for at least one month, comprising administering to the patient once every 1 to 10 days a bolus of purified pro-UK in an amount below that which would induce a systemic effect in the patient, wherein said pro-UK becomes incorporated by the platelets of the patient and remains there for the intravascular life of the intact platelet.

13. The method of claim 12, wherein said pro-UK is administered once every 2 to 5 days for a period of at least 3 months.

* * * * *